United States Patent
Altmann

(10) Patent No.: US 9,763,587 B2
(45) Date of Patent: Sep. 19, 2017

(54) OPERATOR-CONTROLLED MAP POINT DENSITY

(75) Inventor: Andres Claudio Altmann, Haifa (IL)

(73) Assignee: BIOSENSE WEBSTER (ISRAEL), LTD., Yokneam (IL)

(*) Notice: Subject to any disclaimer, the term of this patent is extended or adjusted under 35 U.S.C. 154(b) by 1257 days.

(21) Appl. No.: 12/797,703

(22) Filed: Jun. 10, 2010

(65) Prior Publication Data

US 2011/0306896 A1 Dec. 15, 2011

(51) Int. Cl.
| | |
|---|---|
| *G06K 9/00* | (2006.01) |
| *A61B 5/00* | (2006.01) |
| *A61B 5/053* | (2006.01) |
| *A61B 5/04* | (2006.01) |
| *A61B 5/0402* | (2006.01) |
| *G06T 19/00* | (2011.01) |

(52) U.S. Cl.
CPC ........ *A61B 5/04011* (2013.01); *A61B 5/0402* (2013.01); *A61B 5/6852* (2013.01); *G06T 19/003* (2013.01); *G06T 2210/36* (2013.01); *G06T 2210/41* (2013.01)

(58) Field of Classification Search
CPC ....... A61B 5/743; A61B 5/7435; A61B 5/044; A61L 35/743; A61L 35/7435; G06T 2210/36; G06T 2210/41; G06T 2211/404
USPC ......................................................... 600/547
See application file for complete search history.

(56) References Cited

U.S. PATENT DOCUMENTS

| | | | |
|---|---|---|---|
| 4,751,643 A * | 6/1988 | Lorensen .............. | G06T 7/0081 378/901 |
| 5,391,199 A | 2/1995 | Ben-Haim | |
| 5,443,489 A | 8/1995 | Ben-Haim | |
| 5,558,091 A | 9/1996 | Acker et al. | |
| 5,944,022 A | 8/1999 | Nardella et al. | |
| 5,983,126 A | 11/1999 | Wittkampf | |
| 5,987,345 A * | 11/1999 | Engelmann .......... | G06F 19/321 128/920 |
| 6,172,499 B1 | 1/2001 | Ashe | |
| 6,177,792 B1 | 1/2001 | Govari et al. | |
| 6,456,864 B1 | 9/2002 | Swanson et al. | |
| 6,690,963 B2 | 2/2004 | Ben-Haim et al. | |

(Continued)

FOREIGN PATENT DOCUMENTS

| | | |
|---|---|---|
| CN | 101051387 A | 10/2007 |
| CN | 101249019 A | 8/2008 |

(Continued)

OTHER PUBLICATIONS

AU Examination Report AU2011202361 dated May 30, 2014.

(Continued)

*Primary Examiner* — Michael C Stout
(74) *Attorney, Agent, or Firm* — Notaro, Michalos & Zaccaria P.C.

(57) ABSTRACT

A method includes accepting from a medical imaging system a plurality of map points, each map point including a respective coordinate on a surface of a body organ measured by bringing a medical probe into proximity with the surface. An operator input, which specifies a spatial density at which the map points are to be displayed, is accepted. A subset of the map points is selected responsively to the operator input. The surface is visualized at the specified spatial density by displaying the selected subset of the map points.

14 Claims, 4 Drawing Sheets

(56) References Cited

U.S. PATENT DOCUMENTS

| | | | |
|---|---|---|---|
| 6,788,967 B2 | 9/2004 | Ben-Haim et al. | |
| 6,944,494 B2* | 9/2005 | Forrester | A61B 1/042 600/478 |
| 7,024,024 B1* | 4/2006 | Aiazian | A61B 8/461 382/128 |
| 7,155,042 B1* | 12/2006 | Cowan | A61B 5/055 382/128 |
| 7,379,531 B2* | 5/2008 | Esham | A61N 5/1049 378/210 |
| 7,670,297 B1 | 3/2010 | Hauck et al. | |
| 7,693,563 B2* | 4/2010 | Suresh | G06F 19/3437 382/128 |
| 7,855,723 B2 | 12/2010 | Preiss et al. | |
| 7,974,674 B2* | 7/2011 | Hauck | A61B 5/6885 600/374 |
| 8,036,495 B2* | 10/2011 | Takeshima | G06T 3/4069 348/607 |
| 8,463,007 B2* | 6/2013 | Steinberg | G06T 7/0022 378/4 |
| 2001/0013866 A1* | 8/2001 | Migdal | G06T 17/20 345/423 |
| 2002/0167518 A1* | 11/2002 | Migdal | G06T 17/20 345/428 |
| 2003/0028090 A1 | 2/2003 | Raghavan et al. | |
| 2003/0120156 A1* | 6/2003 | Forrester | A61B 1/042 600/473 |
| 2004/0122332 A1* | 6/2004 | Macadam | A61B 5/042 600/515 |
| 2005/0113674 A1* | 5/2005 | Salla | A61B 5/7289 600/413 |
| 2006/0020213 A1* | 1/2006 | Whitman | A61B 1/05 600/478 |
| 2006/0064007 A1* | 3/2006 | Comaniciu | A61B 8/463 600/416 |
| 2006/0159323 A1* | 7/2006 | Sun | A61B 5/0035 382/128 |
| 2006/0262994 A1* | 11/2006 | Patera | G06T 3/4084 382/276 |
| 2006/0263338 A1 | 11/2006 | Jacoby | |
| 2007/0055142 A1* | 3/2007 | Webler | A61B 5/06 600/425 |
| 2007/0185404 A1* | 8/2007 | Hauck | A61B 5/6885 600/509 |
| 2007/0223794 A1* | 9/2007 | Preiss | A61B 8/12 382/128 |
| 2007/0270705 A1* | 11/2007 | Starks | A61B 5/0402 600/523 |
| 2007/0299351 A1 | 12/2007 | Harlev et al. | |
| 2007/0299353 A1* | 12/2007 | Harlev | A61B 5/0422 600/509 |
| 2008/0249424 A1* | 10/2008 | Harlev | A61B 5/0422 600/509 |
| 2008/0275336 A1* | 11/2008 | Deschamps | A61B 6/032 600/425 |
| 2009/0003669 A1* | 1/2009 | Parks | A61B 5/037 382/128 |
| 2009/0069704 A1* | 3/2009 | MacAdam | A61B 5/044 600/523 |
| 2009/0099468 A1* | 4/2009 | Thiagalingam | A61B 5/0452 600/515 |
| 2009/0232369 A1* | 9/2009 | Senegas | G06T 7/0012 382/128 |
| 2009/0262109 A1 | 10/2009 | Markowitz et al. | |
| 2009/0264738 A1* | 10/2009 | Markowitz | A61B 5/0422 600/424 |
| 2009/0265128 A1* | 10/2009 | Markowitz et al. | 702/94 |
| 2010/0026687 A1* | 2/2010 | Shankar | G06T 11/60 345/441 |
| 2010/0049032 A1* | 2/2010 | Steinke | G01R 33/481 600/416 |
| 2010/0160768 A1* | 6/2010 | Marrouche | A61B 6/503 600/420 |
| 2010/0160773 A1* | 6/2010 | Cohen | G06T 7/0022 600/424 |
| 2010/0172556 A1* | 7/2010 | Cohen | A61B 6/5217 382/128 |
| 2010/0274123 A1* | 10/2010 | Voth | A61B 5/042 600/424 |
| 2010/0283484 A1* | 11/2010 | Cohen | A61B 5/06 324/649 |
| 2010/0305429 A1* | 12/2010 | Shachar | A61B 5/0538 600/424 |
| 2010/0305433 A1* | 12/2010 | Harlev | A61B 5/0422 600/424 |
| 2011/0021903 A1* | 1/2011 | Strommer | A61B 5/042 600/410 |
| 2011/0028825 A1* | 2/2011 | Douglas | G06F 19/321 600/407 |
| 2011/0038516 A1* | 2/2011 | Koehler | G06T 7/0081 382/128 |
| 2011/0082710 A1* | 4/2011 | Subash | G06F 19/322 705/3 |
| 2011/0152882 A1* | 6/2011 | Wenderow | A61B 5/7475 606/130 |
| 2011/0160574 A1* | 6/2011 | Harlev | A61B 5/0422 600/424 |
| 2012/0035488 A1* | 2/2012 | MacAdam | A61B 5/044 600/509 |
| 2012/0101398 A1* | 4/2012 | Ramanathan | A61B 5/04012 600/523 |

FOREIGN PATENT DOCUMENTS

| | | |
|---|---|---|
| CN | 101568941 A | 10/2009 |
| WO | WO 2007/035306 A2 | 3/2007 |
| WO | WO 2007143085 A2 * | 12/2007 |
| WO | WO 2008/078265 A2 | 7/2008 |

OTHER PUBLICATIONS

AU Examination Report AU2011202361 dated Sep. 2, 2014.
CN Search Report CN201110173541.0 dated Apr. 10, 2014.
CN Search Report CN201110173541.0 dated Apr. 29, 2014.
CN Search Report CN201110173541.0 dated Dec. 10, 2014.
EP Search Report EP114169329 dated Jun. 22, 2016.
Alexa, Marc et al. Point Set Surfaces, IEEE, PI, 2001, pp. 21-29.
Carsten Moenning et al. Intrinsic Point Cloud Simplification, Computer Laboratory, Univ. of Cambridge, Graphicon 2004, pp. 1-16.
Casella M. et al. Right Ventricular Substrate Mapping Using the Ensite NAVX System: Accuracy of High-Density Voltage Map Obtained by Automatic Point Acquisition During Geometry Reconstruction. Cardiac Arrhythmia and Heart Failure research Center, 2009 Heart Rhythm Society, vol. 6, No. 11, pp. 1598-1605.
Dey, T. K. et al. Decimating Samples for Mesh Simplification, Proceedings of the 13$^{th}$ Canadian Conference on Computational Geometry 2001, pp. 1-4.
Eitel, C. et al. Device Profile: Ensite Velocity Cardiac Mapping System: A New Platform for 3D Mapping of Cardiac Arrhythmias. 2010 Expert Reviews Ltd., vol. 7, No. 2, pp. 185-192.
Kitago, M. et al. Efficient and Prioritized Point Subsampling for CSRBF Compression. Eurographics symposium on Point-Based Graphics 2006, The Eurographics Association Symposium on Point-Based Graphics, pp. 1-9.
Wilson, K. et al. Dynamic Cardiac Mapping on Patient-Specific Cardiac Models. Imaging Research Laboratories, Computer Science, 2008, pp. 967-974.

* cited by examiner

US 9,763,587 B2

OPERATOR-CONTROLLED MAP POINT DENSITY

FIELD OF THE INVENTION

The present invention relates generally to medical imaging, and specifically to visualizing a surface of a body organ.

BACKGROUND OF THE INVENTION

In electrophysiological diagnostic procedures (e.g., intracardiac electrical mapping), an invasive medical probe is introduced into a cavity of a body organ. As the probe is positioned at specific points within the organ, the probe measures specific information (e.g., an electrical potential) and conveys the measurements to a mapping system. The mapping system creates a map comprising the measurements at their respective locations in the organ. The map can be used in applying various diagnostic and therapeutic procedures to the organ.

SUMMARY OF THE INVENTION

An embodiment of the present invention that is described herein provides a method, including:

accepting from a medical imaging system a plurality of map points, each map point including a respective coordinate on a surface of a body organ measured by bringing a medical probe into proximity with the surface;

accepting an operator input specifying a spatial density at which the map points are to be displayed;

selecting a subset of the map points responsively to the operator input; and visualizing the surface at the specified spatial density by displaying the selected subset of the map points.

In some embodiments, each map point includes a respective value of a tissue property measured by the medical probe at the respective coordinate, and visualizing the surface includes displaying respective values of the tissue property at the selected subset of map points. In some embodiments, the tissue property includes at least one property type selected from a group of types consisting of an electrical potential, a Local Activation Time (LAT), a tissue impedance, a tissue mechanical property, a force applied to the surface by the probe and an ablation parameter. In an embodiment, the method includes retaining the plurality of map points in a memory irrespective of selection of the subset.

In a disclosed embodiment, the operator input specifies one or more regions of the surface, and selecting the subset and visualizing the surface include choosing the subset and displaying the surface at the specified spatial density only within the specified regions. In an embodiment, the regions include at least first and second regions, the operator input specifies first and second spatial densities, different from one another, and selecting the subset and visualizing the surface include choosing the subset and displaying the surface in the first and second regions at the respective first and second spatial densities.

In another embodiment, the operator input specifies one or more map points that are not to be visualized, and selecting the subset includes substituting the one or more map points with respective other map points, while preserving the specified spatial density. In yet another embodiment, selecting the subset includes choosing the map points that are distributed uniformly over the surface. In still another embodiment, selecting the subset includes choosing the map points that are closest to a three-dimensional envelope defined by the plurality of map points.

There is additionally provided, in accordance with an embodiment of the present invention, apparatus, including:

a first interface, which is configured to accept from a medical imaging system a plurality of map points, each map point including a respective coordinate on a surface of a body organ measured by bringing a medical probe into proximity with the surface;

a second interface, with is configured to accept an operator input specifying a spatial density at which the map points are to be displayed; and a processor, which is configured to select a subset of the map points responsively to the operator input, and to visualize the surface at the specified spatial density by displaying the selected subset of the map points.

There is further provided, in accordance with an embodiment of the present invention, a computer software product, including a non-transitory computer-readable medium, in which program instructions are stored, which instructions, when read by a computer, cause the computer to accept from a medical imaging system a plurality of map points, each map point including a respective coordinate on a surface of a body organ measured by bringing a medical probe into proximity with the surface, to accept an operator input specifying a spatial density at which the map points are to be displayed, to select a subset of the map points responsively to the operator input, and to visualize the surface at the specified spatial density by displaying the selected subset of the map points.

The present invention will be more fully understood from the following detailed description of the embodiments thereof, taken together with the drawings in which:

DETAILED DESCRIPTION OF EMBODIMENTS

Overview

Physiological or anatomical mapping procedures typically create a map comprising map points collected from a medical imaging system. Each map point comprises a respective coordinate within a body organ, and possibly a physiological property collected by a medical probe at the respective coordinate. The physiological property is typically measured by a medical probe that is brought in close proximity to a surface of the body organ. The map is displayed to an operator, e.g., a medical professional.

In many cases, it is advantageous to display the map points at a high density, so as to give the operator a better sense of the quality and sampling density of the map. In some scenarios, however, the operator may find that the density of the displayed map points is too high. For example, the operator may find that a large number of map points on the map, at least in a given region, obscures information pertinent to the procedure. Such a scenario may occur, for example, when using probes having multiple mapping electrodes, although the disclosed techniques are not limited to such cases.

Embodiments of the present invention that are described hereinbelow provide methods and systems that enable the operator to specify a spatial density at which the map points are to be displayed. The operator may specify the map point density for one or more specific regions of the map, or for the entire map. Once the operator has specified the desired spatial density, a subset of the acquired map points is chosen automatically. The map is then displayed to the operator at the specified density. Several example criteria for automatically selecting the subset of map points are described herein. Typically, the original map points at the initial density are retained in memory, so that the initial (high) spatial density can be reset without data loss.

The methods and systems described herein provide greater control over the mapping and visualization process, thereby enhancing the user-friendliness of the mapping system without compromising accuracy or quality.

System Description

Figure 1:
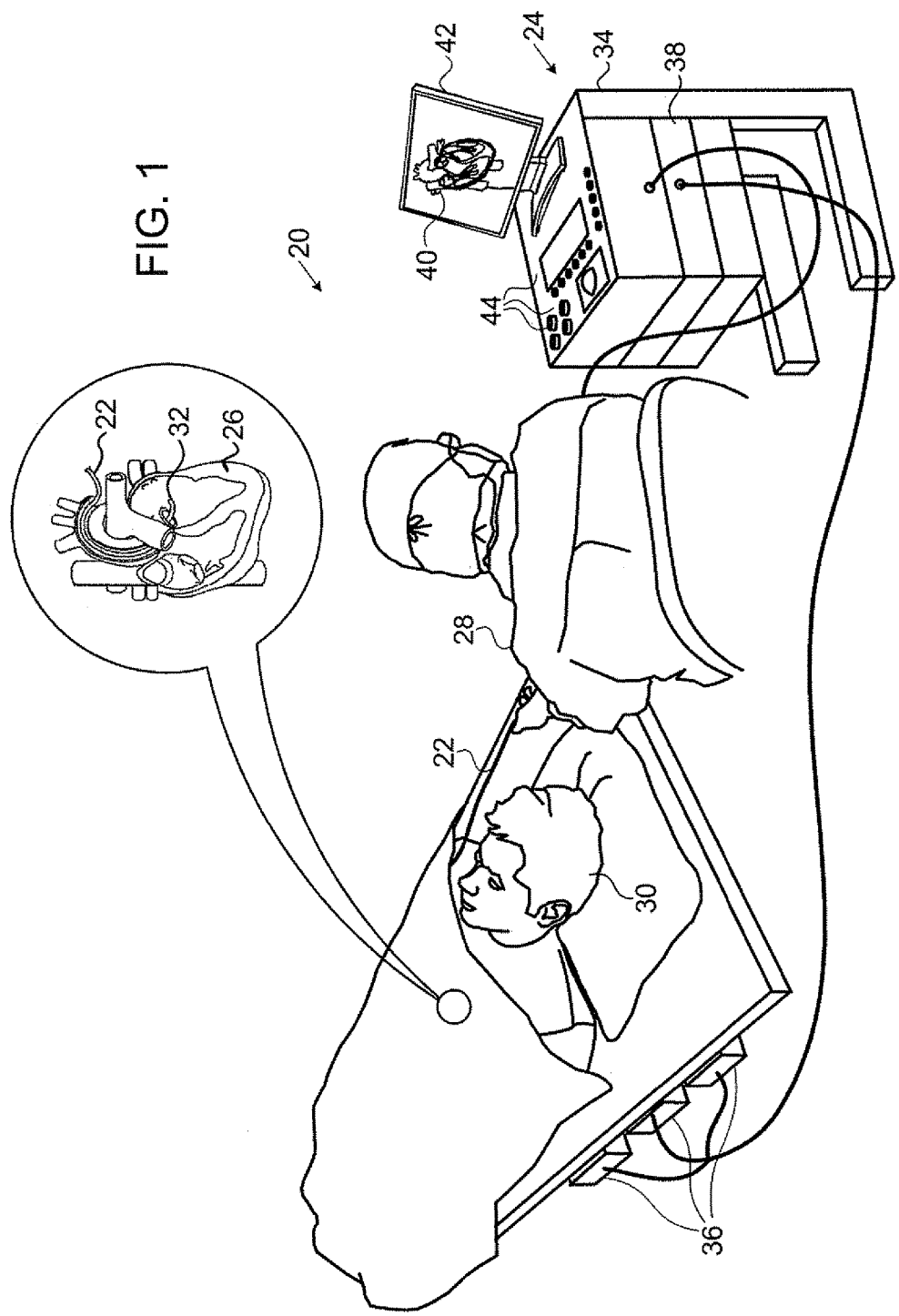
FIG. 1 is a schematic, pictorial illustration of an intracardiac mapping system implementing operator-controlled map point density, in accordance with a disclosed embodiment of the present invention.

FIG. 1 is a schematic, pictorial illustration of an intracardiac mapping system 20 that implements operator-controlled map point density, in accordance with a disclosed embodiment of the present invention. System 20 comprises a probe 22, such as a catheter, and a control console 24. In the embodiment described hereinbelow, it is assumed that probe 22 is used for diagnostic or therapeutic treatment, such as for mapping electrical potentials in a heart 26 of a patient 30. Alternatively, probe 22 may be used, mutatis mutandis, for other therapeutic and/or diagnostic purposes in the heart or in other body organs.

An operator 28 inserts probe 22 through the vascular system of patient 30 so that a distal end 32 of probe 22 enters a chamber of heart 26. System 20 uses magnetic position sensing to determine position coordinates of distal end 32 inside heart 26. Console 24 comprises a driver circuit 34, which drives field generators 36 placed at known positions external to patient 30, e.g., below the patient's torso. A magnetic field transducer (not shown) coupled to distal end 32 of probe 22 generates electrical signals in response to the magnetic fields from the coils, thereby enabling console 24 to determine the position of distal end 32 with in the chamber.

Although in the present example system 20 measures the position of distal end 32 using magnetic-based sensors, other position tracking techniques may be used (e.g., impedance-based sensors). Magnetic position tracking techniques are described, for example, in U.S. Pat. Nos. 5,391,199, 5,443, 489, 6,788,967, 6,690,963, 5,558,091, 6,172,499, 6,177,792, whose disclosures are incorporated herein by reference. Impedance-based position tracking techniques are described, for example, in U.S. Pat. Nos. 5,983,126, 6,456, 864 and 5,944,022, whose disclosures are incorporated herein by reference.

In order to map the cardiac chamber in question, operator 28 positions distal end 32 at multiple positions on (or in close proximity to) the inner surface of the chamber. At each position, an electrode (not shown) coupled to the distal end measures a certain physiological property, in the present example the local surface electrical potential. System 20 correlates the position measurements and the electrical potential measurements. Thus, the system collects multiple map points, with each map point comprising a coordinate on the inner chamber surface and a respective electrical potential measurement at this coordinate.

Console 24 comprises a processor 38, which produces and displays a map 40 showing the acquired map points. Thus, map 40 (also referred to as an electrical map) visualizes the distribution of electrical potentials over the surface of the heart chamber. Processor 38 displays map 40 to operator 28 using a display 42. Using a group of input devices 44, operator 28 can manipulate map 40 on the display. In particular, operator 28 can control the density at which the map points are displayed, as will be explained below.

Processor 38 typically comprises a general-purpose computer, with suitable front end and interface circuits for receiving signals from probe 22 and controlling the other components of console 24. Processor 38 may be programmed in software to carry out the functions that are described herein. The software may be downloaded to console 24 in electronic form, over a network, for example, or it may be provided on non-transitory tangible media, such as optical, magnetic or electronic memory media. Alternatively, some or all of the functions of processor 38 may be carried out by dedicated or programmable digital hardware components, or using a combination of hardware and software elements.

Figure 2:
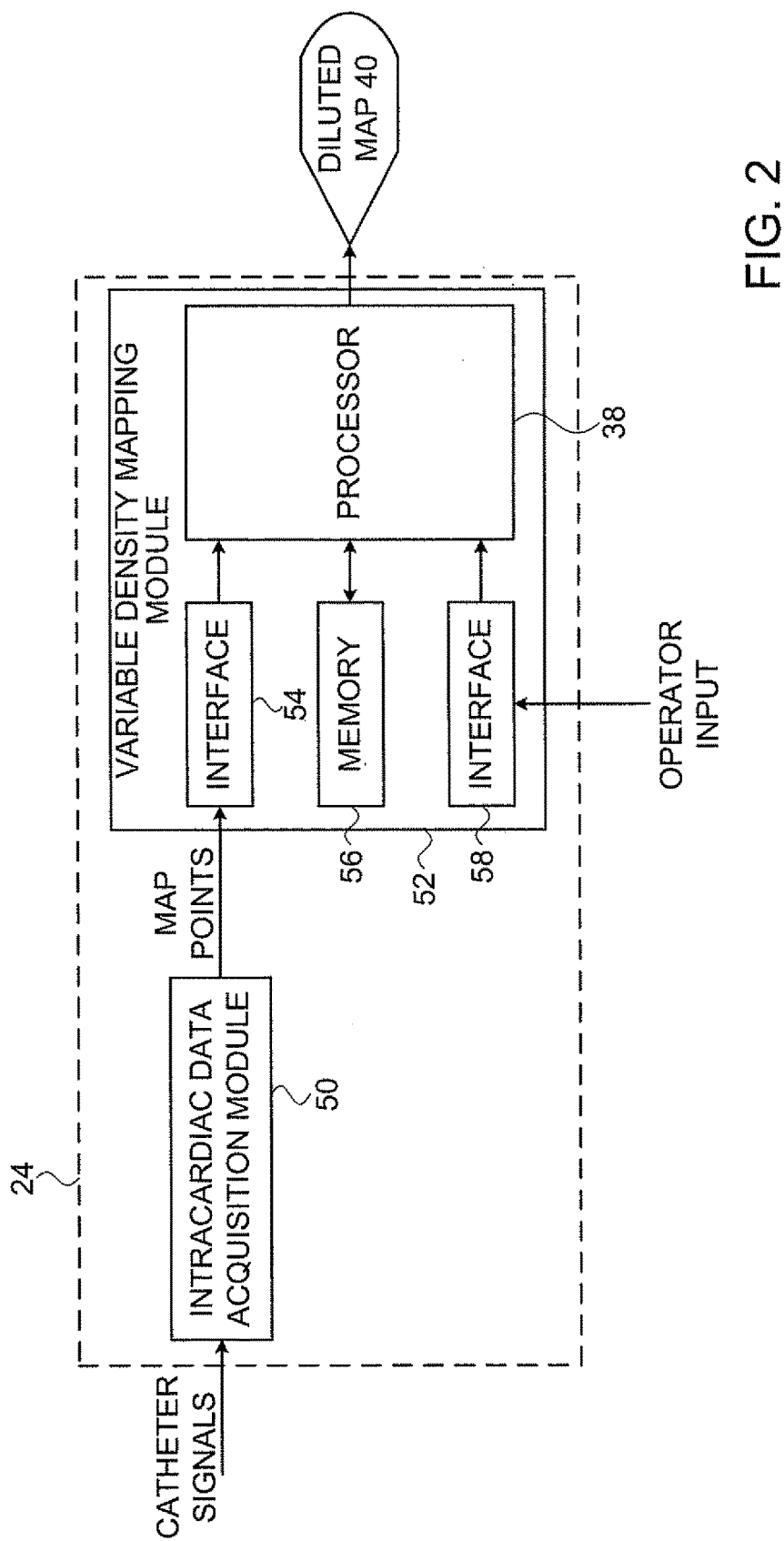
FIG. 2 is a block diagram that schematically illustrates elements of an intracardiac mapping system implementing operator-controlled map point density, in accordance with a disclosed embodiment of the present invention.

FIG. 2 is a block diagram that schematically illustrates elements of console 24, in accordance with a disclosed embodiment of the present invention. An intracardiac data acquisition module 50 receives and processes electrical potential measurements and position signals from probe 22. Module 50 converts the signals received from the probe into map points, and transmits the map points to a variable-density mapping module 52. Each map point comprises a location coordinate on the surface of the heart chamber and an electrical potential measured at this coordinate.

Processor 38 collects the map points from an interface 54, and generates an initial electrical map comprising all the collected map points. Processor 38 typically stores the collected map points in a memory 56, and presents the initial map on display 42. Memory 56 may comprise any suitable volatile and/or non-volatile memory, such as random access memory or a hard disk drive. Processor 38 also receives operator input from input devices 44 via an interface 58. The operator input specifies a diluted (i.e., lower) map point density value for the map. In some embodiments, the operator input also specifies a selected region of the initial map, which is to be displayed at the diluted map point density. Based on the operator input, processor 38 creates a diluted electrical map having the specified map point density. Processor 38 displays the diluted map to operator 28 on display 42, and may also store the diluted map in memory 56.

Variable Density Map Generation

As discussed supra, the methods and systems described herein enable operator 28 to specify a lower spatial density for displaying the map points of the electrical map. After operator 28 specifies the desired map point density, processor 38 automatically selects a subset of the acquired map points, which have the specified spatial density. Processor 38 may use any suitable criteria for selecting the subset of map points. For example, processor 38 may select map points that provide a roughly uniform coverage. As another example, processor 38 may select map points that are closest to a three-dimensional envelope defined by the initial map. As noted above, processor 38 may perform this process for the entire map, or for one or more regions of the map that are specified by the operator.

In some embodiments, processor 38 may present on display a user interface, which enables operator 28 to control (using input devices 44) the map point density of map 40 or parts thereof. Additionally or alternatively, the user interface may permit operator 28 to select unwanted map points shown on the map currently being displayed, using input devices 44. Processor 38 then removes the selected points and automatically substitutes them with other map points, so as to maintain the desired map point density.

Figure 3:
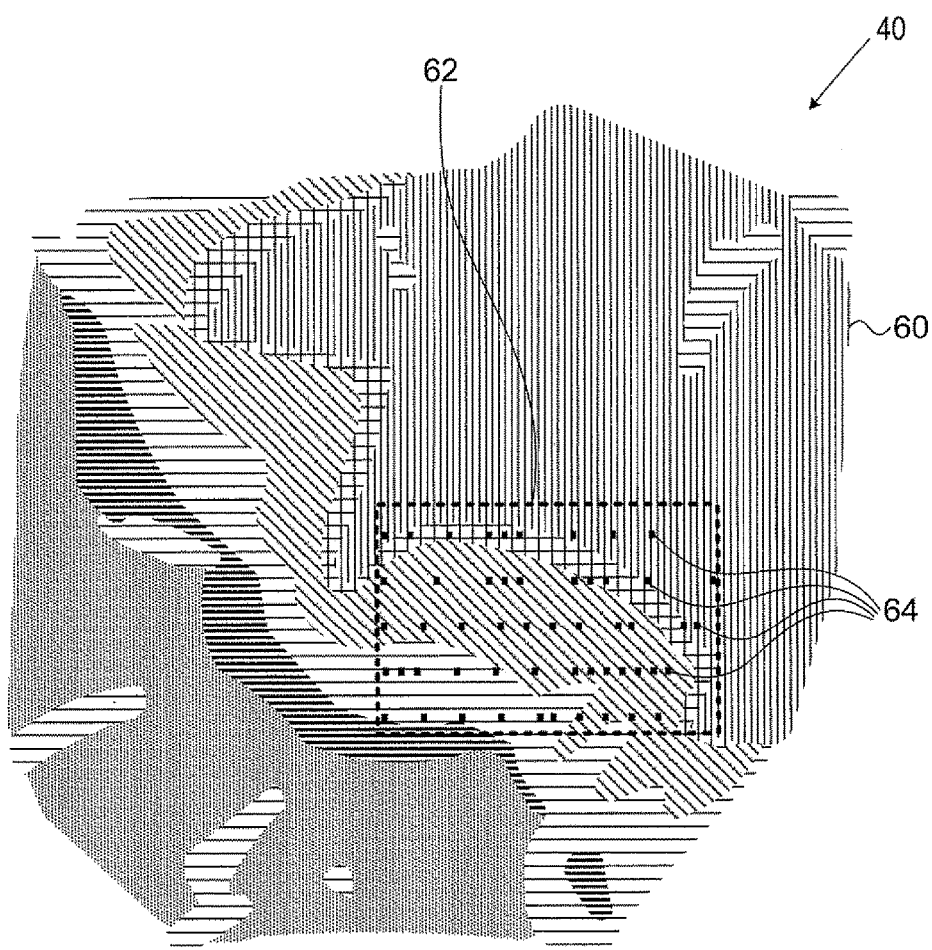
FIG. 3 is an illustration of an example electrical map of a cardiac chamber, in accordance with a disclosed embodiment of the present invention.

FIG. 3 is a schematic illustration of an example intracardiac electrical map 40, in accordance with a disclosed embodiment of the present invention. Map 40 initially comprises an initial map 60, comprising all the map points collected by probe 22. Different electrical potential levels are visualized in FIG. 3 using different shading patterns. In a real-life system, different potentials can be visualized, for example, using different colors or using any other suitable graphical features.

A region 62 is selected by operator 28 for display at a lower map point density. Region 62 comprises a plurality of map points 64 that are automatically selected by processor 38 and have the lower map point density. Presenting region 62 at a lower map point density may provide operator 28 with a clearer representation of the electrical potentials in the region, in comparison with displaying the region at the original map point density.

Figure 4:
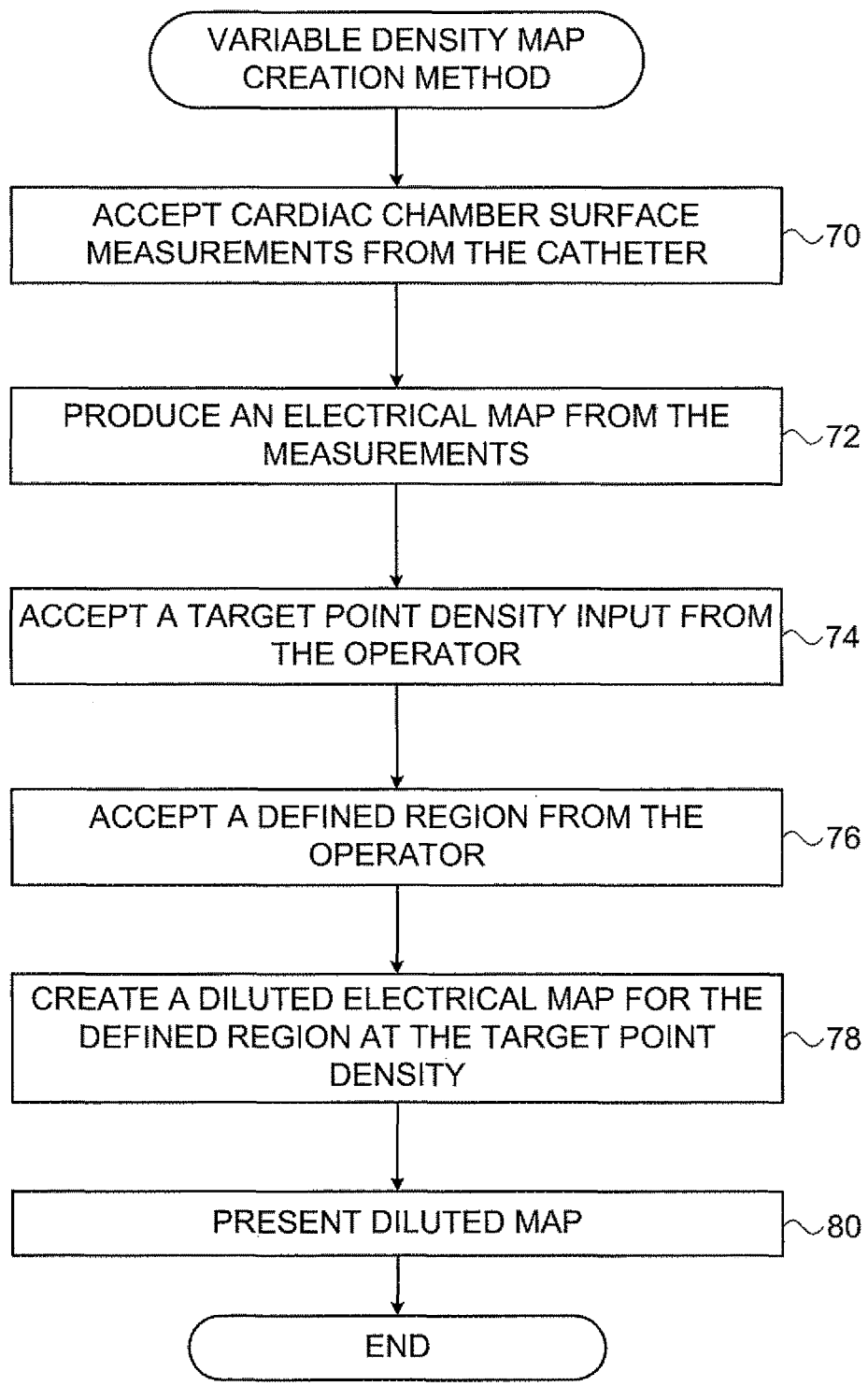
FIG. 4 is a flow diagram that schematically illustrates a method for producing an electrical map having an operator-controlled map point density, in accordance with a disclosed embodiment of the present invention.

FIG. 4 is a flow diagram that schematically illustrates a method for producing an electrical map having an operator-controlled map point density, in accordance with a disclosed embodiment of the present invention. Processor 38 accepts from probe 22 location and electrical potential measurements acquired at respective locations on the inner surface of a cardiac chamber (step 70). Using the collected measurements, processor 38 generates a plurality of map points, i.e., an initial map of electrical potentials for the chamber of heart 26 (step 72). Processor 38 stores the map points in memory 56 and presents the initial electrical map on display 42.

Using input devices 44, operator 28 specifies a desired map point density (step 74). For example, operator 28 may enter the point density directly, select a map point density from a predefined list presented on the display, or specify the desired density using any other means. In some embodiments, operator 28 also selects, using input devices 44, one or more regions (e.g., region 62 shown in FIG. 3) that are to be displayed using the specified map point density (step 76). Generally, operator 28 may select multiple regions that are either contiguous or not contiguous. Alternatively, operator 28 can specify the map point density for the entire map. If operator 28 selects multiple regions, the operator can specify a different density for each region, or identical densities for two or more of the regions.

Processor 38 creates a diluted map, which has the specified density at the selected region or regions (step 78). The processor generates the diluted map by selecting a subset of the initial map points having the specified density. The processor stores the diluted map in memory 56, and presents the diluted map on display 42 to operator 28 (step 80). In some embodiments memory 56 may store multiple versions of the electrical map (including the initial map), with each version having a different point density. Using input devices 44, operator 28 can toggle between the versions.

In some embodiments, the method of FIG. 4 is performed in real time, i.e., concurrently with or shortly after performing the measurements by probe 22. In alternative embodiments, the method of FIG. 4 is performed off-line, i.e., applied to a pre-acquired and stored set of initial map points.

The embodiments described herein refer mainly to electrical maps that visualize electrical potentials, such as unipolar and bi-polar voltages. In alternative embodiments, the disclosed techniques can be used to process map points that visualize any other tissue property that is measured by the probe at respective locations in the body, such as, for example, tissue Local Activation Time (LAT), tissue impedance, tissue mechanical properties such as strain. Additionally or alternatively, the disclosed techniques can be used to process map points that visualize properties that are related to the measurement or to the medical procedure in question, such as the force exerted by the probe on the tissue, contact information and ablation parameters. Further alternatively, the map points may comprise only coordinates without any physiological properties, such as when conducting anatomical mapping of an organ.

The corresponding structures, materials, acts, and equivalents of all means or steps plus function elements in the claims below are intended to include any structure, material, or act for performing the function in combination with other claimed elements as specifically claimed. The description of the present disclosure has been presented for purposes of illustration and description, but is not intended to be exhaustive or limiting to the disclosure in the form disclosed. Many modifications and variations will be apparent to those of ordinary skill in the art without departing from the scope and spirit of the disclosure. The embodiment was chosen and described in order to best explain the principles of the disclosure and the practical application, and to enable others of ordinary skill in the art to understand the disclosure for various embodiments with various modifications as are suited to the particular use contemplated.

It is intended that the appended claims cover all such features and advantages of the disclosure that fall within the spirit and scope of the present disclosure. As numerous modifications and changes will readily occur to those skilled in the art, it is intended that the disclosure not be limited to the limited number of embodiments described herein. Accordingly, it will be appreciated that all suitable variations, modifications and equivalents may be resorted to, falling within the spirit and scope of the present disclosure.

What is claimed is:

1. A method of measuring and displaying electrical surface potentials on a surface of a heart, the method comprising the steps of:

providing a display, a processor, and an input device;

providing a vascular probe comprising (a) a position sensor configured to generate electrical signals indicative of a position coordinate of a distal end of the probe, and further comprising (b) an electrode at the distal end of the probe which is configured to measure an electrical potential of the surface of the heart at the position coordinate;

contacting the surface of the heart with the probe at a plurality of points;

the processor receiving the electrical signals from the probe and determining both the position coordinate of the distal end of the probe, and the electrical potential measurement of the surface of the heart at the position coordinate, for each of the plurality of points;

(i) using the processor, producing an initial map of the surface of the heart using all of the plurality of points, said map which includes all of the points on the heart contacted by the probe being at a first spatial density;

(ii) displaying the initial map comprising all of the points on said display at the first spatial density, including by depicting the electrical potential measurement of the surface of the heart on the display for each of the respective points;

(iii) after the initial map is produced, and using the input device: receiving operator input including selecting at least a first sub-region, a second sub-region, and optionally additional sub-regions, the sub-regions each corresponding to different respective areas of the initial map as shown on the display;

(iv) after the initial map is produced, and using the input device: receiving further operator input comprising a first sub-region density, a second sub-region density, and optionally additional sub-region densities, said sub-region densities each being map point densities which are lower than said first spatial density;

(v) after receiving said operator input, generating a diluted map using the processor and displaying the diluted map on the display, wherein when the diluted map is displayed:

the first sub-region is displayed at the first sub-region density, comprising displaying only a subset of the points on the corresponding areas of heart surface which were contacted by the probe and which were displayed in the corresponding portion of the initial map;

the second sub-region is displayed at the second sub-region density, comprising displaying only a subset of the points on the corresponding areas of heart surface which were contacted by the probe and which were displayed in the corresponding portion of the initial map;

areas which were part of the initial map but which do not fall within any sub-region identified by the operator at step (iii) are displayed at the first spatial density; and the diluted map comprises a single continuous image of at least part of the heart on the display, where different areas of said single continuous image are simultaneously displayed at the first sub-region density, the second sub-region density, and the first spatial density.

2. The method according to claim 1, further comprising wherein the map point data further comprises at least one property type selected from a group of types consisting of a Local Activation Time (LAT), a tissue impedance, a tissue mechanical property, a force applied to the surface by the probe, and an ablation parameter.

3. The method according to claim 1, further comprising retaining in a memory all of the plurality of points at the first spatial density after generating the diluted map; and after generating the diluted map and displaying the diluted map on the display, receiving operator input requesting the initial map and, in response to the request, again displaying the initial map comprising all of the points on the display.

4. The method according to claim 1, further comprising wherein the operator input specifies one or more points that are not to be within the selected subset, and wherein the processor is configured to substitute the one or more points with respective other points, while preserving the specified spatial density.

5. The method according to claim 1, further comprising selecting the subset of points to display in the diluted map for at least one of the first sub-region and the second sub-region by choosing points that are distributed uniformly over the surface.

6. The method according to claim 1, further comprising selecting the subset of points to display in the diluted map for at least one of the first sub-region and the second sub-region by choosing points that are closest to a three-dimensional envelope defined by all of the plurality of points at the first spatial density.

7. An apparatus for measuring and displaying electrical surface potentials of a surface of a body organ, the apparatus comprising:

a probe comprising a position sensor, and an electrode at a distal end thereof, the probe being configured to generate electrical signals indicative of a position coordinate of the distal end of the probe and an electrical potential measurement of the surface of the body organ at the position coordinate;

a display;

an input device; and a console comprising a processor and operatively linked to the display, the input, device, and the probe;

the apparatus being configured wherein:

the processor is configured to receive electrical signals from the probe when the probe is in contact with a series of body organ surfaces, and to determine map point data comprising both the position coordinate of the distal end of the probe and the electrical potential measurement of the surface of the body organ at each position coordinate, for each of a plurality of points on said body organ;

the apparatus being further configured to (i) using the processor, produce an initial map of the surface of the body organ using all of the plurality of points received from the probe, said map being at a first spatial density;

(ii) display the initial map comprising all of the points on said display at the first spatial density, including by depicting the electrical potential measurement of the surface of the body organ on the display for each of the respective points;

(iii) using the input device, receive operator input including selecting at least a first sub-region and a second sub-region, the sub-regions each corresponding to different respective areas of the initial map as shown on the display;

(iv) using the input device, receive further operator input comprising a first sub-region density and a second sub-region density, said sub-region densities each being map point densities which are lower than said first spatial density;

(v) in response to said operator input, generate a diluted map using the processor and displaying the diluted map on the display, wherein when the diluted map is displayed:

the first sub-region is displayed at the first sub-region density, comprising displaying only a subset of the points on the corresponding areas of body organ surface which were contacted by the probe and which were displayed in the corresponding portion of the initial map;

the second sub-region is displayed at the second sub-region density, comprising displaying only a subset of the points on the corresponding areas of body organ surface which were contacted by the probe and which were displayed in the corresponding portion of the initial map;

areas which were part of the initial map but which do not fall within either the first sub-region or the second sub-region are displayed at the first spatial density, including displaying all of the points which were contacted by the probe in the respective portions of the body organ; and the diluted map comprises a single continuous image of at least part of the body organ on the display, where different areas of said single continuous image are simultaneously displayed at the first sub-region density, the second sub-region density, and the first spatial density.

8. The apparatus according to claim 7, wherein the map point data comprises at least one additional tissue property selected from a group of types consisting of a Local Activation Time (LAT), a tissue impedance, a tissue mechanical property, a force applied to the surface by the probe and an ablation parameter.

9. The apparatus according to claim 7, wherein the console further comprises a memory configured to retain all of the plurality of points at the first spatial density after generation of the diluted map.

10. The apparatus according to claim 7, wherein the operator input specifies one or more points that are not to be within the selected subset, and wherein the processor is configured to substitute the one or more points with respective other points, while preserving the specified spatial density.

11. The apparatus according to claim 7, wherein the processor is configured to select the subset of points to display in the diluted map for at least one of the first sub-region and the second sub-region by choosing points that are distributed uniformly over the surface.

12. The apparatus according to claim 7, wherein the processor is configured to select the subset of points to display in the diluted map for at least one of the first sub-region and the second sub-region by choosing points that are closest to a three-dimensional envelope defined by all of the plurality of points at the first spatial density.

13. A computer software product for use with a computer comprising a processor, the computer being operatively linked to a display, an input device, and a medical probe having a position sensor and an electrode configured for measuring electrical surface potentials;

the computer software product comprising a non-transitory computer-readable medium, in which program instructions are stored, which instructions, when read by a computer operatively linked to said input display, input device, and probe:

cause the processor to receive electrical signals from the probe when the probe is in contact with a series of body organ surfaces, and to determine map point data comprising both the position coordinate of the distal end of the probe and the electrical potential measurement of the surface of the body organ at each position coordinate, for each of a plurality of points on said body organ;

the instructions further causing the computer to:

(i) using the processor, produce an initial map of the surface of the body organ using all of the plurality of points received from the probe, said map being at a first spatial density;

(ii) cause display of the initial map comprising all of the points on said display at the first spatial density, including by depicting the electrical potential measurement of the surface of the body organ on the display for each of the respective points;

(iii) using the input device, receive operator input including selecting a first sub-region, and optionally also a second sub-region, the sub-regions each corresponding to different respective areas of the initial map as shown on the display;

(iv) using the input device, receive further operator input comprising a first sub-region density, and optionally also a second sub-region density, said sub-region densities each being map point densities which are lower than said first spatial density;

(v) in response to said operator input, generate a diluted map using the processor and display the diluted map on the display, wherein when the diluted map is displayed according to said instructions:

the first sub-region is displayed at the first sub-region density, comprising displaying only a subset of the points on the corresponding areas of body organ surface which were contacted by the probe and which were displayed in the corresponding portion of the initial map;

the second sub-region, when selected, is displayed at the second sub-region density, comprising displaying only a subset of the points on the corresponding areas of body organ surface which were contacted by the probe and which were displayed in the corresponding portion of the initial map; and areas which were part of the initial map but which do not fall within any of said sub-regions are displayed at the first spatial density, including displaying all of the points which were contacted by the probe in the respective portions of the body organ.

14. The computer software product of claim 13, wherein said instructions cause the computer to receive operator instructions selecting a second sub-region, and selecting a corresponding second sub-region density; and wherein said diluted map comprises the second sub-region displayed at the second sub-region density.

* * * * *